(12) United States Patent
Nolan et al.

(10) Patent No.: US 9,066,791 B2
(45) Date of Patent: Jun. 30, 2015

(54) VENTILATION SYSTEM FOR GOGGLES

(75) Inventors: William H. Nolan, Lakewood, CO (US); Stephen B. Katsaros, Denver, CO (US)

(73) Assignee: HaberVision LLC, Golden, CO (US)

( * ) Notice: Subject to any disclaimer, the term of this patent is extended or adjusted under 35 U.S.C. 154(b) by 1222 days.

(21) Appl. No.: 12/534,597

(22) Filed: Aug. 3, 2009

(65) Prior Publication Data
US 2010/0024099 A1 Feb. 4, 2010

Related U.S. Application Data

(60) Provisional application No. 61/085,784, filed on Aug. 1, 2008.

(51) Int. Cl.
B08B 15/00 (2006.01)
A61F 9/02 (2006.01)

(52) U.S. Cl.
CPC ...................................... *A61F 9/028* (2013.01)

(58) Field of Classification Search
CPC ............ A61F 9/028; A42B 3/28; F24F 13/20
USPC ............. 415/108; 248/220.21, 220.22; 2/436; 454/370
See application file for complete search history.

(56) References Cited

U.S. PATENT DOCUMENTS

| | | | | |
|---|---|---|---|---|
| 3,825,953 A * | 7/1974 | Hunter | ................................ | 2/437 |
| 4,150,443 A * | 4/1979 | McNeilly | ............................ | 2/436 |
| 4,229,855 A * | 10/1980 | Rowe | ................................ | 16/29 |
| 4,443,893 A * | 4/1984 | Yamamoto | ......................... | 2/436 |
| 4,893,356 A * | 1/1990 | Waters | .............................. | 2/171.3 |
| 5,193,347 A | 3/1993 | Apisdorf | | |
| 5,203,425 A * | 4/1993 | Wehmeyer | ........................ | 182/19 |
| 5,283,914 A | 2/1994 | James | | |
| 5,452,480 A * | 9/1995 | Ryden | ................................ | 2/436 |
| 5,533,500 A | 7/1996 | Her-Mou | | |
| 5,966,746 A * | 10/1999 | Reedy et al. | ........................ | 2/436 |
| 6,038,707 A * | 3/2000 | Ryden et al. | ........................ | 2/436 |
| 6,049,917 A * | 4/2000 | Ryden | ................................ | 2/436 |
| 6,081,929 A | 7/2000 | Rothrock et al. | | |
| 6,122,773 A | 9/2000 | Katz | | |
| 6,470,696 B1 | 10/2002 | Palfy et al. | | |
| 6,704,944 B2 * | 3/2004 | Kawainshi et al. | ................ | 2/436 |
| 6,810,610 B2 * | 11/2004 | Hardman et al. | ................ | 37/407 |
| 6,834,509 B2 * | 12/2004 | Palfy et al. | ....................... | 62/140 |
| 7,802,318 B2 * | 9/2010 | Chen | ................................ | 2/171.3 |
| 8,021,039 B2 * | 9/2011 | Amato | ........................... | 374/141 |
| 2005/0132468 A1 * | 6/2005 | Lundgren | ....................... | 2/171.3 |

(Continued)

FOREIGN PATENT DOCUMENTS

EP 268549 B1 10/1990
JP 2001-055617 A 2/2001

(Continued)

OTHER PUBLICATIONS

PCT International Search Report and Written Opinion mailed May 4, 2010; International Application No. PCT/US2009/060904, 10 pages.

*Primary Examiner* — Steven B McAllister
*Assistant Examiner* — Jonathan Cotov
(74) *Attorney, Agent, or Firm* — Kilpatrick Townsend & Stockton LLP

(57) ABSTRACT

The present ventilation system for goggles includes a fan wherein the system is readily and removably attached to the goggles.

18 Claims, 15 Drawing Sheets

(56) References Cited

U.S. PATENT DOCUMENTS

2006/0048286 A1 3/2006 Donato
2007/0113324 A1* 5/2007 Chen ................................ 2/424
2008/0173612 A1* 7/2008 Renz ............................ 215/260
2010/0095439 A1 4/2010 Nolan et al.

FOREIGN PATENT DOCUMENTS

| JP | 2001-303353 A | 10/2001 |
| JP | 2005-179795 A | 7/2005 |

* cited by examiner

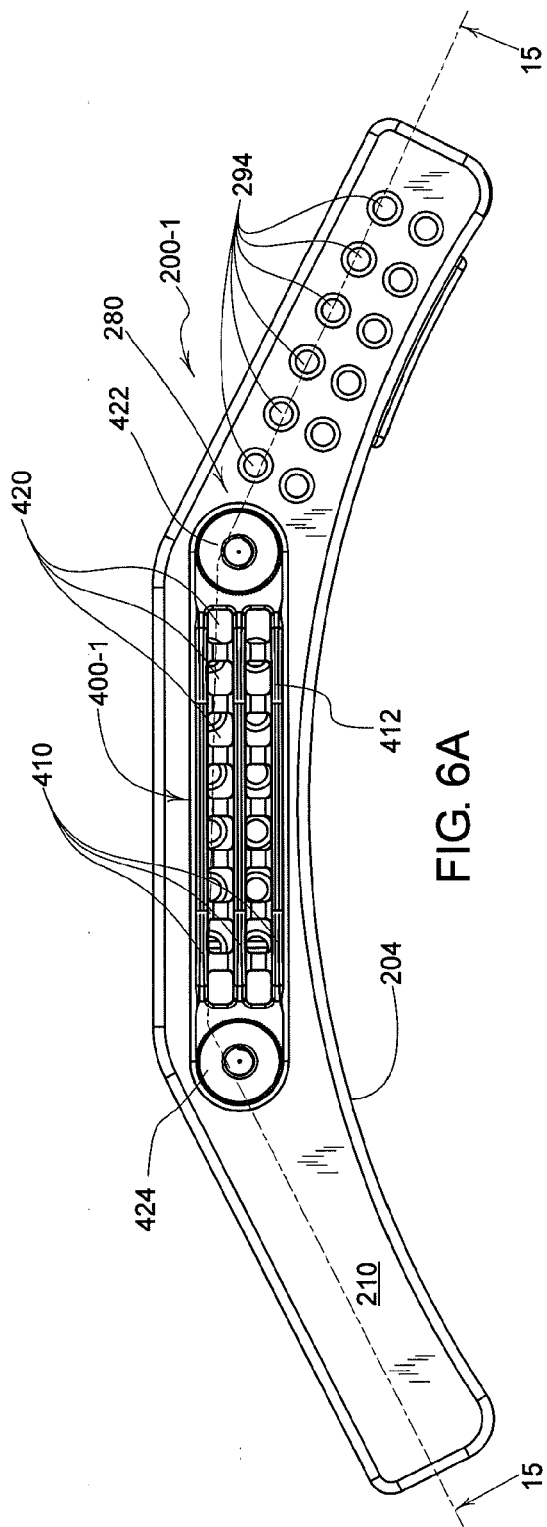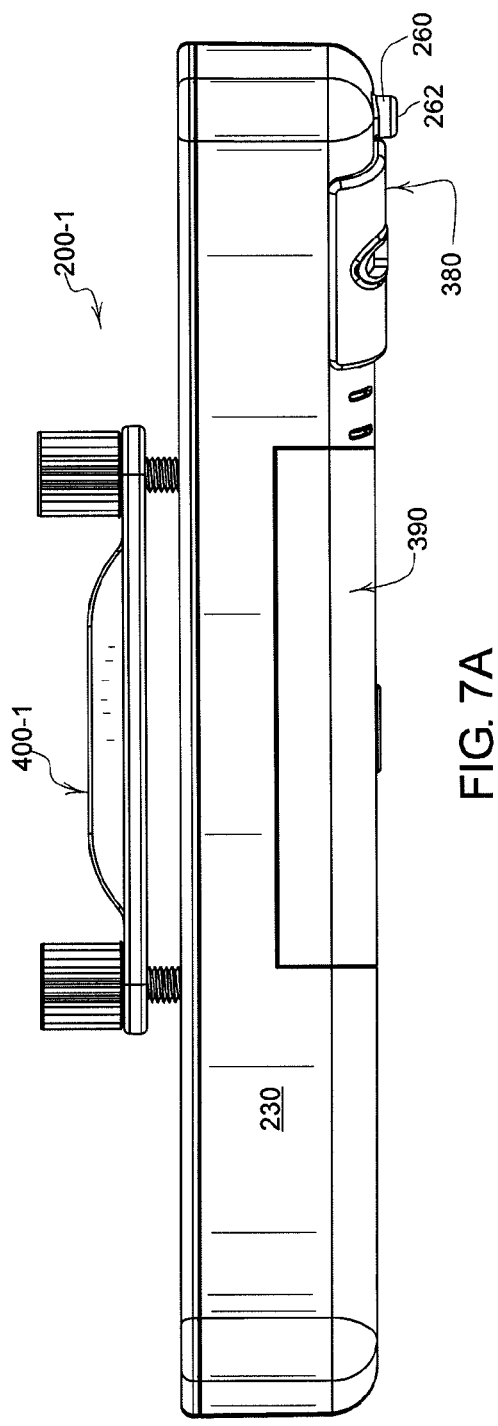

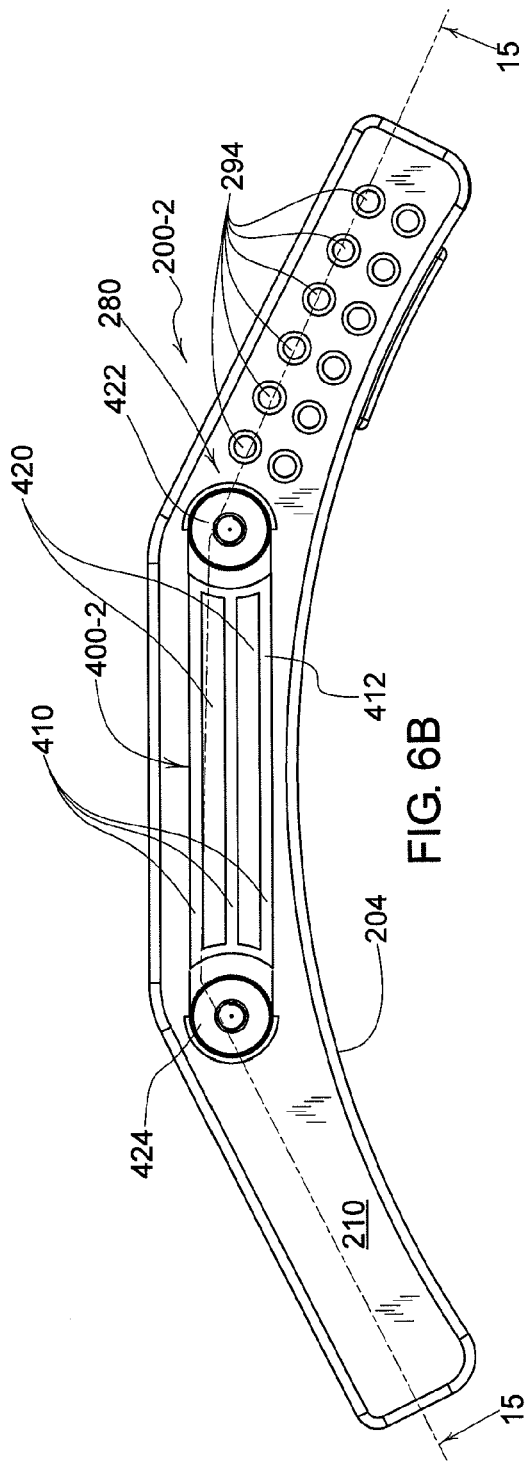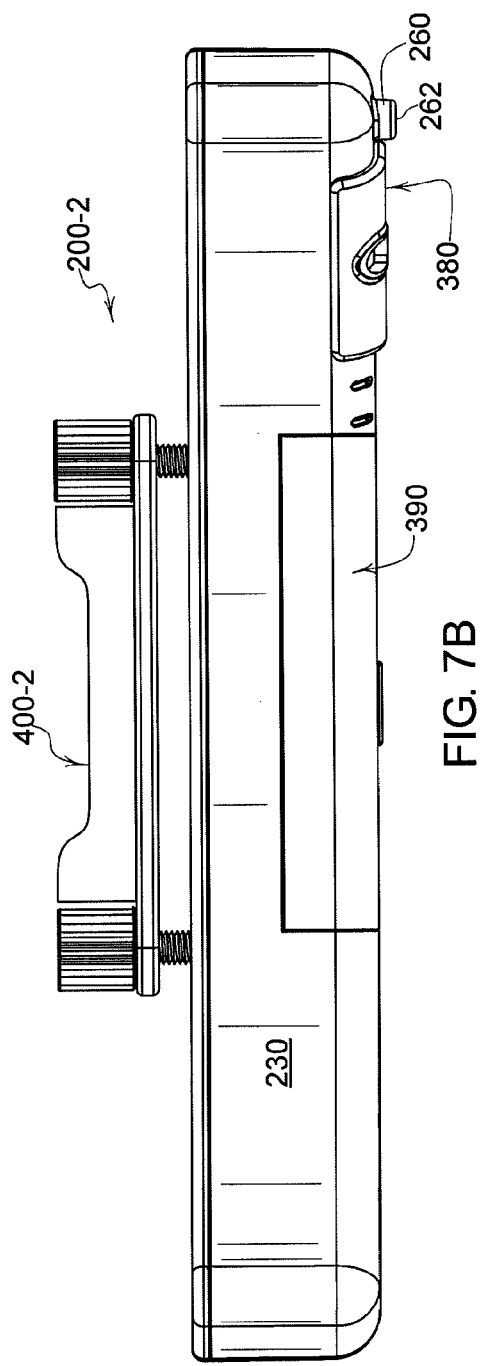

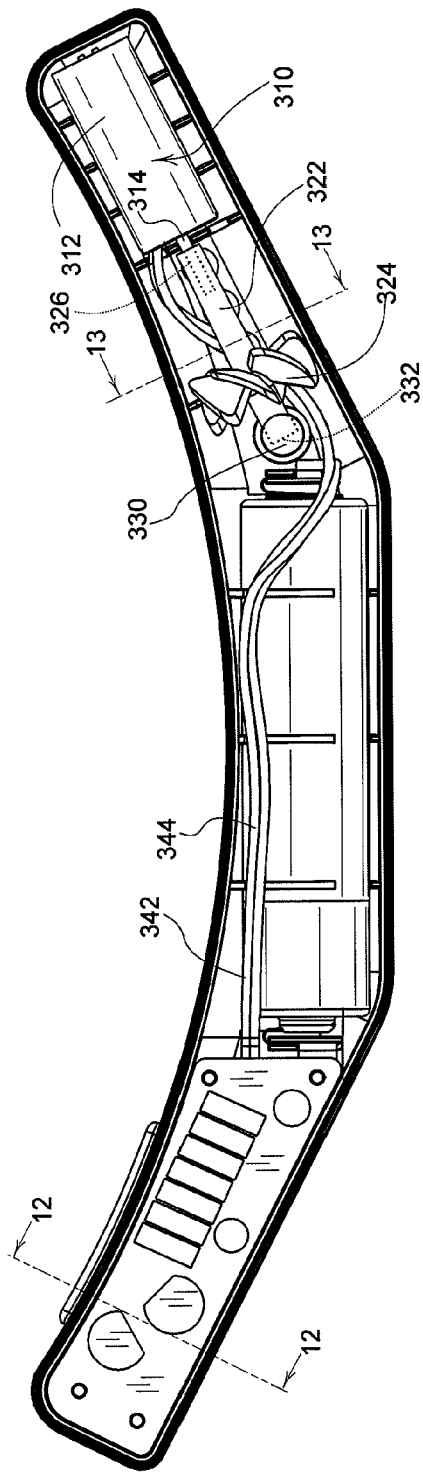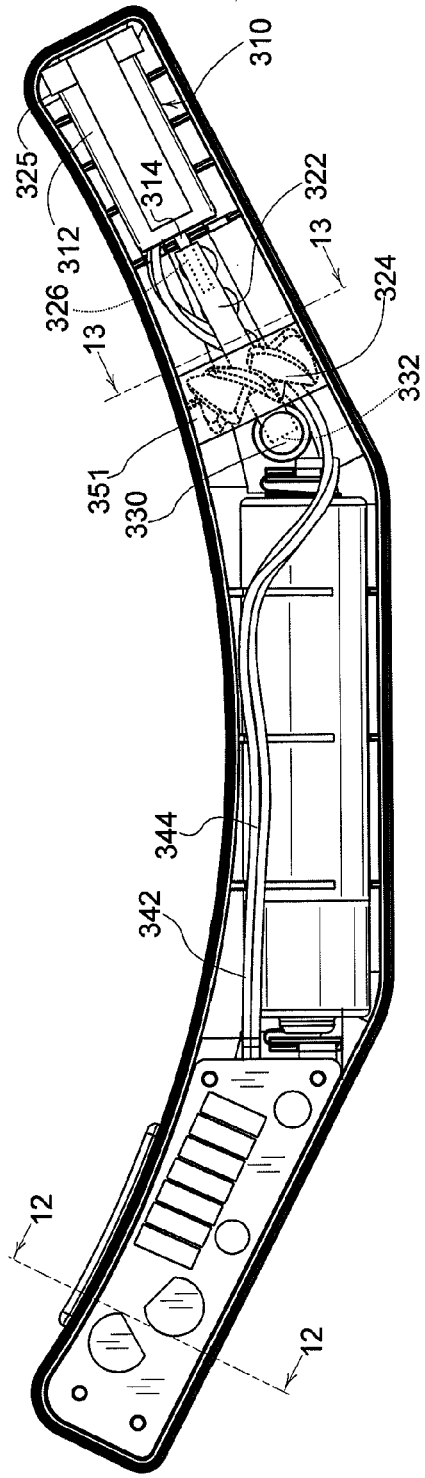

VENTILATION SYSTEM FOR GOGGLES

This application claims the benefit of and is a non-provisional of U.S. Provisional Application No. 61/085,784 filed on Aug. 1, 2008, which is incorporated by reference in its entirety for all purposes.

BACKGROUND OF THE INVENTION

Goggles or safety glasses are forms of protective eyewear that usually enclose or protect the eye area in order to prevent particulates, water or chemicals from striking the eyes. They are used in chemistry laboratories, in woodworking and sports; they are often used in winter sports (e.g. skiing) or summer sports (e.g., motocross). Goggles are often worn when using power tools such as drills or chainsaws to prevent flying particles from damaging the eyes. Many types of goggles are available as prescription goggles for those with vision problems.

The central issue being addressed with the present device is goggle lens fogging, therefore the reader will benefit from an examination of the causes of goggle lens fogging and to eyeglass lens fogging when such eyeglasses is worn under goggles. Any surface will accumulate water vapor when the temperature of the surface is lower than the dew point temperature of the adjacent air. In a ski or motor sports goggles environment, lens temperature and dew point are both subject to frequent change which may result in lens fogging. Two sources of water vapor increase the goggles interior void dew point temperature (the "Dew Point") above that generally prevailing in the athlete's absence: the athlete's face, including the eyes, tears therefrom, the skin and the exhaled breath. Ventilation of the goggles interior void by rapid athlete motion causes lens temperature to fall. Exhaled breath readily enters the interior void within modern goggles due to the air pervious nature of the frame. When the athlete is in motion, the air stream around the athlete head tends to force exhaled breath into goggles and results in intermittent lens fogging. Additionally, in very cold weather the athlete is likely to wear protective garments about the nose and mouth, which channels the athlete's exhaled breath into the goggles.

BRIEF SUMMARY OF THE INVENTION

This invention relates to the field of eyewear for protecting a user's eyes.

Various configurations of goggles ventilation systems are described in the patents, while others are simply commercially available. While the patented and commercially available devices fulfill their respective and particular objects and requirements, they do not describe ventilation system for goggles that provides the advantages of the present invention as described later herein.

In one exemplary embodiment, a ventilation system for readily and removably attaching to a frame of goggles is disclosed. The ventilation system an enclosure and an attachment system. The enclosure houses a fan and battery. The attachment system readily and removably attaches the ventilation system enclosure to the frame.

In another exemplary embodiment disclosed herein, a method of attaching a ventilation system to goggles, the method including at least: providing the ventilation system including at least: a threaded post; providing the goggle including at least: frame defining a top plate; and foam disposed on the top plate; piercing the foam with the threaded post after the providing the ventilation system and the providing the goggles; and capturing the goggles frame with the threaded post after the piercing.

In another exemplary embodiment disclosed herein, a ventilation system for goggles including at least: a first distal end section; a second distal end section oppositely disposed from the first distal end; a middle section between the first and second distal end sections; an intake formed in the first distal end section; and a humidity sensor adjacent to the second distal end section.

BRIEF DESCRIPTION OF THE DRAWINGS

The following figures of the drawings show exemplary embodiments of the present ventilation system for goggles:

FIGS. 6A and 6B show top plan views of the ventilation system embodiments of FIGS. 5A and 5B;

FIGS. 7A and 7B show back elevation views of the ventilation system embodiments of FIGS. 5A and 5B;

FIGS. 11A and 11B show top plan views of the ventilation system embodiments of FIGS. 5A and 5B with an enclosure top removed therefrom;

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

In general terms, the present ventilation system 200 for goggles 100 is capable of exhausting humid air from an interior portion of the goggles 100 and replacing the humid air with fresh air.

Having provided a brief overview of what the utility of the present ventilation system 200, a basic description of goggles 100, the ventilation system 200 and specific operation thereof will now be provided. It should be noted that the following is considered as illustrative only of the principles of the ventilation system 200 for goggles 100. Further, since numerous modifications and changes will readily occur to those skilled in the art, it is not desired to limit the ventilation system 200 for goggles 100 to the exact construction and operation shown and described, and accordingly, all suitable modifications and equivalents may be resorted to, falling within the scope of the ventilation system 200 for goggles 100.

Figure 1:
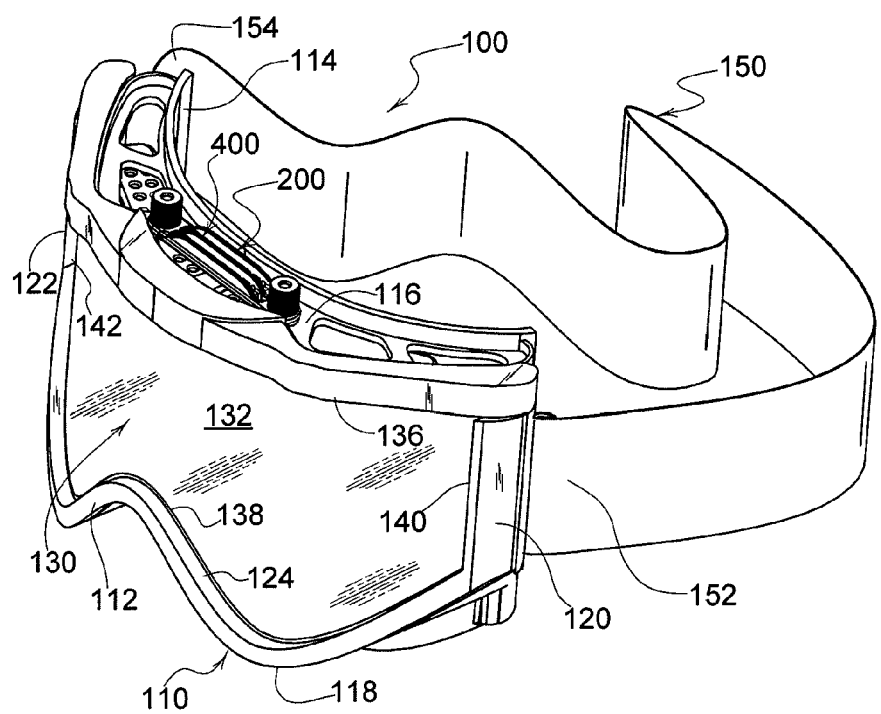
FIG. 1 shows an isometric perspective of goggles provided with a ventilation system interfaced therewith.

Eyewear, such as goggles 100 illustrated in FIGS. 1 thru 4 are utilized for protecting the user's eyes. With reference to FIG. 1 showing goggles 100 in an isometric perspective, is commonly used to improve the user's vision and overall comfort during a given activity (e.g., skiing or motorsports). The goggles 100 are provided with a frame 110, a lens 130 and a strap 150. The frame 110 can be made of any of a variety of materials such as thermoplastic polyurethane and is commonly made of a material that has a low durometer so it can conform to the user's face. The frame 110 is provided with a front surface 112 and an oppositely disposed back surface 114. The frame 110 is also provided with a top 116, a bottom 118 a left side 120 and a right side 122. The top 116, bottom 118 left side 120 and right side 122 have thickness thereby causing the front surface 112 to be offset from the back surface 114. The frame 110 may be provided with a foam (not shown) attached to the back surface 114 for improving the fit when interfaced with the face of the user. In one exemplary configuration, the frame 110 is provided with a channel 124 extends around a perimeter defined by the top 116, the bottom 118, the left side 120 and the right side 122. This channel 124 is capable of receiving the lens 130 and holding the lens 130 relative to the frame 110.

Figure 2:
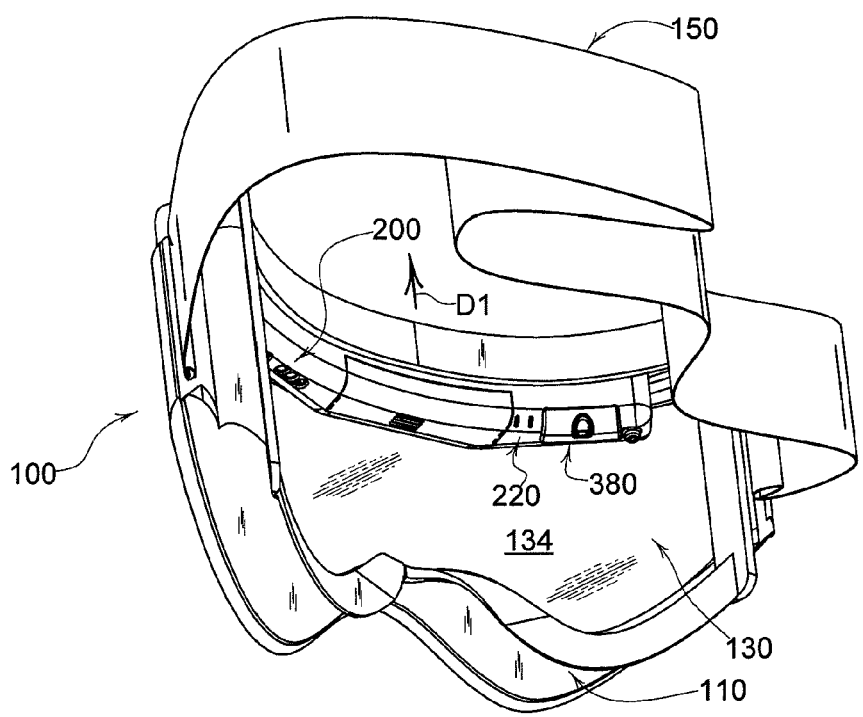
FIG. 2 shows an isometric perspective of a back side of goggles of FIG. 1.
Figure 3:
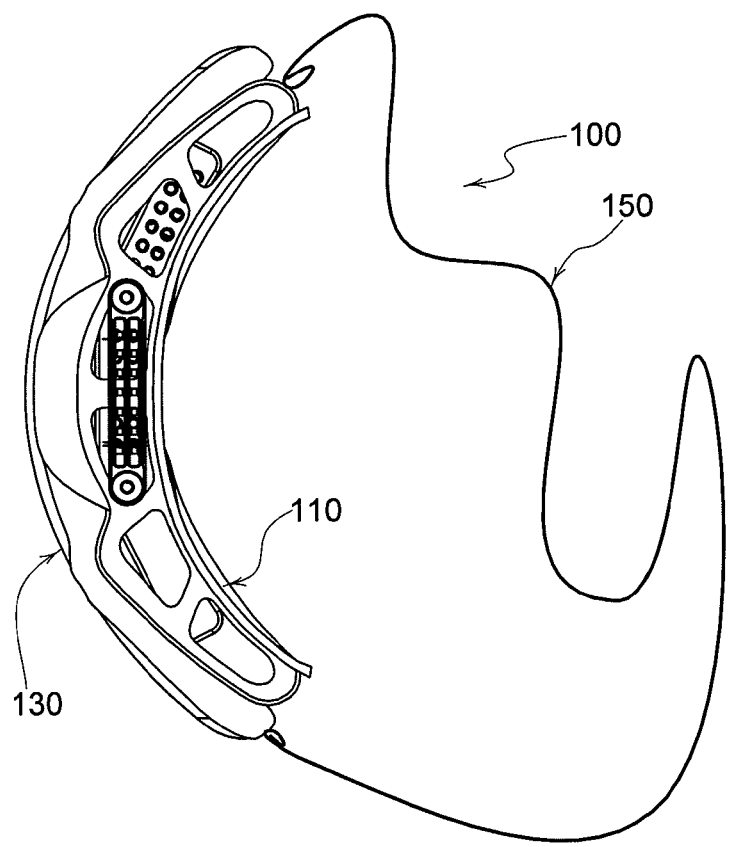
FIG. 3 shows a top plan view of goggles provided with a ventilation system of FIG. 1.
Figure 4:
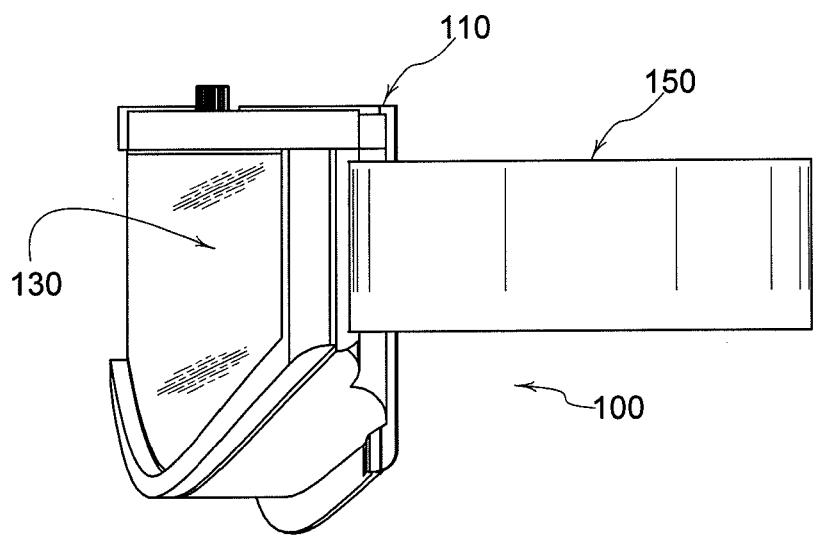
FIG. 4 shows a side elevation view of the goggles provided with a ventilation system of FIG. 1.

With continued reference to FIG. 1, the lens 130 is provided with a front surface 132 and an oppositely disposed back surface 134 (FIG. 2). The surfaces 132, 134 are defined at their perimeter by a top 136, a bottom 138, a left side 140 and a right side 142. The lens 130 may be provided as a single layer lens, or as a dual layer lens having a void between the two layers. Additionally, the lens 130 is made of a material that is relatively translucent (e.g. polycarbonate).

With continued reference to FIG. 1, the goggles 100 are provided with a strap 150 defining a left distal end 152 and an oppositely disposed right distal end 154. The left distal end 152 is attached to the frame 110 and the left side 120 and the right distal end 154 is attached to the frame right side 122.

Figure 5A:
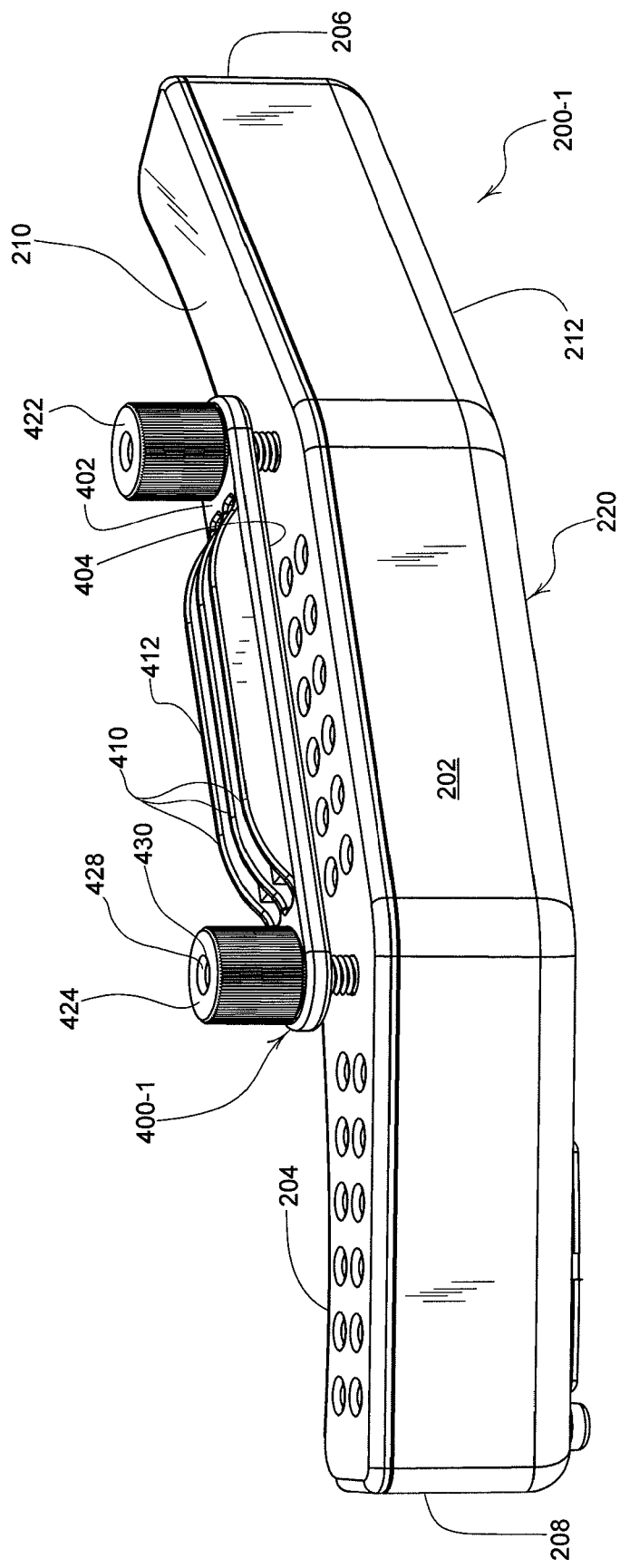
FIGS. 5A and 5B show isometric perspective views of exemplary embodiments of a ventilation system for goggles.

With reference to FIGS. 5A thru 8 showing various views of embodiments of a ventilation system 200, the ventilation system 200 is provided for improving the functionality of the goggles 100 by improving circulation of air across the lens back surface 134 (FIG. 2). With reference to FIG. 5A showing a perspective view of a first embodiment of the ventilation system 200-1, the ventilation system 200 is provided with a front 202, a back 204, a left side 206, a right side 208, a top 210 and a bottom 212. As illustrated in FIG. 1, when interfaced with the goggles 100, the top 210 of the ventilation system 200 is adjacent to an interior surface of the top 116 of the frame 110. FIG. 5B shows a different configuration for the bridge 400-2 in a second embodiment. FIGS. 5A, 6A, 7A, 9A and 11A depict a first embodiment of the ventilation system 200-1 and FIGS. 5A, 6A, 7A, 9A and 11A depict a second embodiment of the ventilation system 200-2. The details of the differences between these two embodiments are detailed herein.

The depicted embodiments use screws to removably attach the ventilation system 200 to goggles 100, but other embodiments could use glue, tape, Velcro™, and/or magnets. Velcro, tape or glue could be used to bond the top 210 of the ventilation system 200 to the interior surface of the top 116 of the frame 110. For magnet attachment, the top 210 of the ventilation system 200 could have a magnetic metal and magnets on an exterior surface of the top 116 of the frame 110 could be used to removably attach the ventilation system 200 to goggles 100. Of course, the magnet could be switched with the magnetic metal in other embodiments. Still other embodiments could include a clip integral to the goggle 100 should goggles be pre-designed to accept the ventilation system 200. Embodiments could even make the ventilation system 200 integral to the goggle 100 and built-into its frame 110.

Figure 9A:
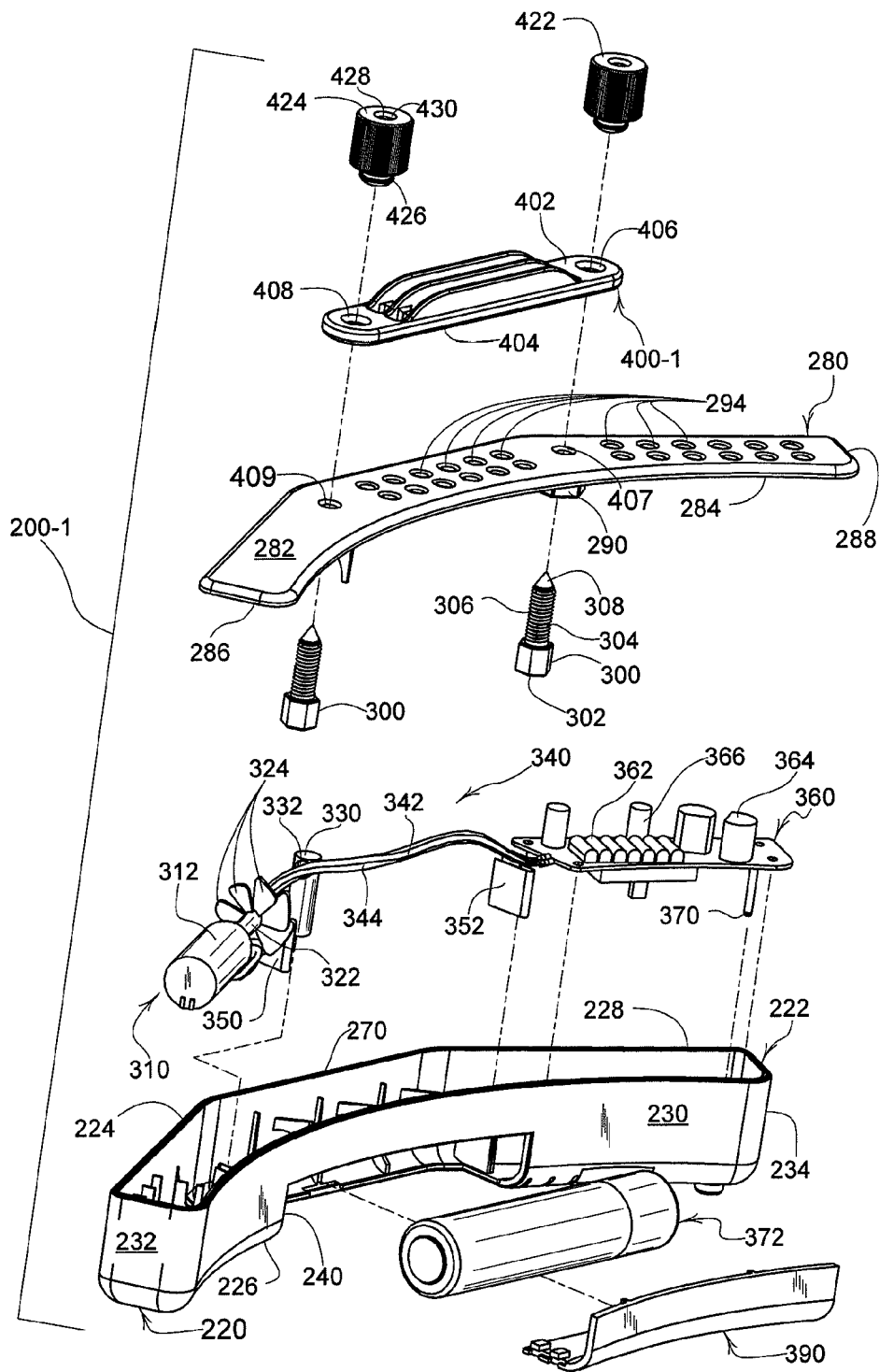
FIGS. 9A and 9B show perspective views of the ventilation system embodiments of FIGS. 5A and 5B in an exploded condition.
Figure 9B:
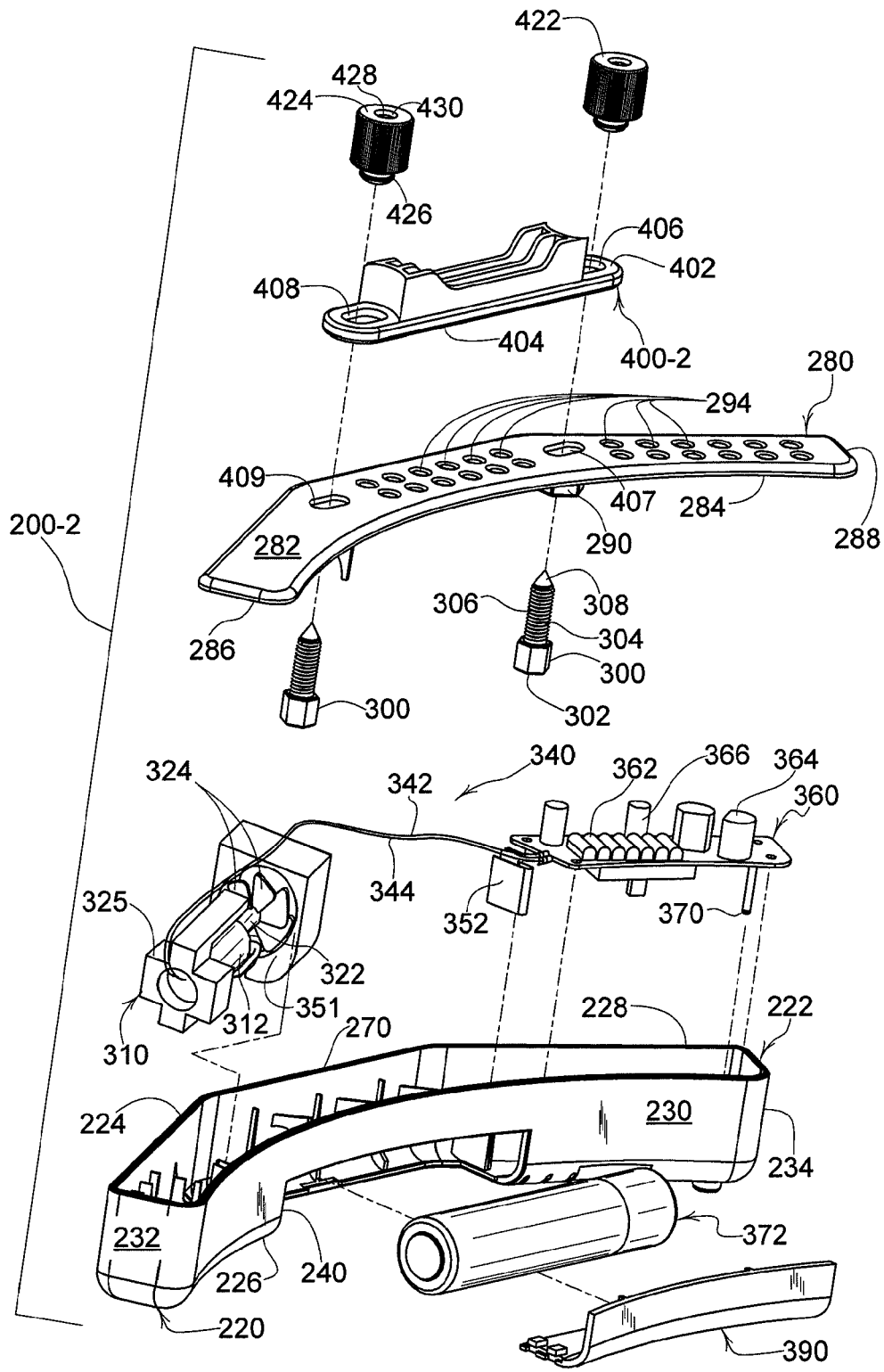

With reference to FIGS. 9A and 9B showing perspective views on exemplary embodiments of the ventilation system 200 in an exploded condition, the ventilation system 200 is provided with an enclosure 220 (FIG. 2) including a base 222, a top 280 and a battery cover 390. The base 222 is provided with a top 224, a bottom 226, a front 228, a back 230, a left side 232 and a right side 234 configured as illustrated in FIGS. 9A and 9B. The base 222 is also provided with a battery opening 240 formed in the back 230 and the bottom 226.

In comparison to the embodiment of the ventilation system 200-1 of FIG. 9A, the embodiment of the ventilation system 200-2 of FIG. 9B has differences. The motor 312 has a retaining element 325 bonded to the motor 312 that holds it stationary within the enclosure 220 with a press fit. The fan blade 324 is arranged in a shroud 351 that separates a first chamber from a second chamber. The rotation of the fan blade 324 creates a pressure differential that moves air between the chambers. One chamber is in pressure communication with the intake ports 250 such that air is sucked into the enclosure 220 through the intake ports 250.

Figure 10:
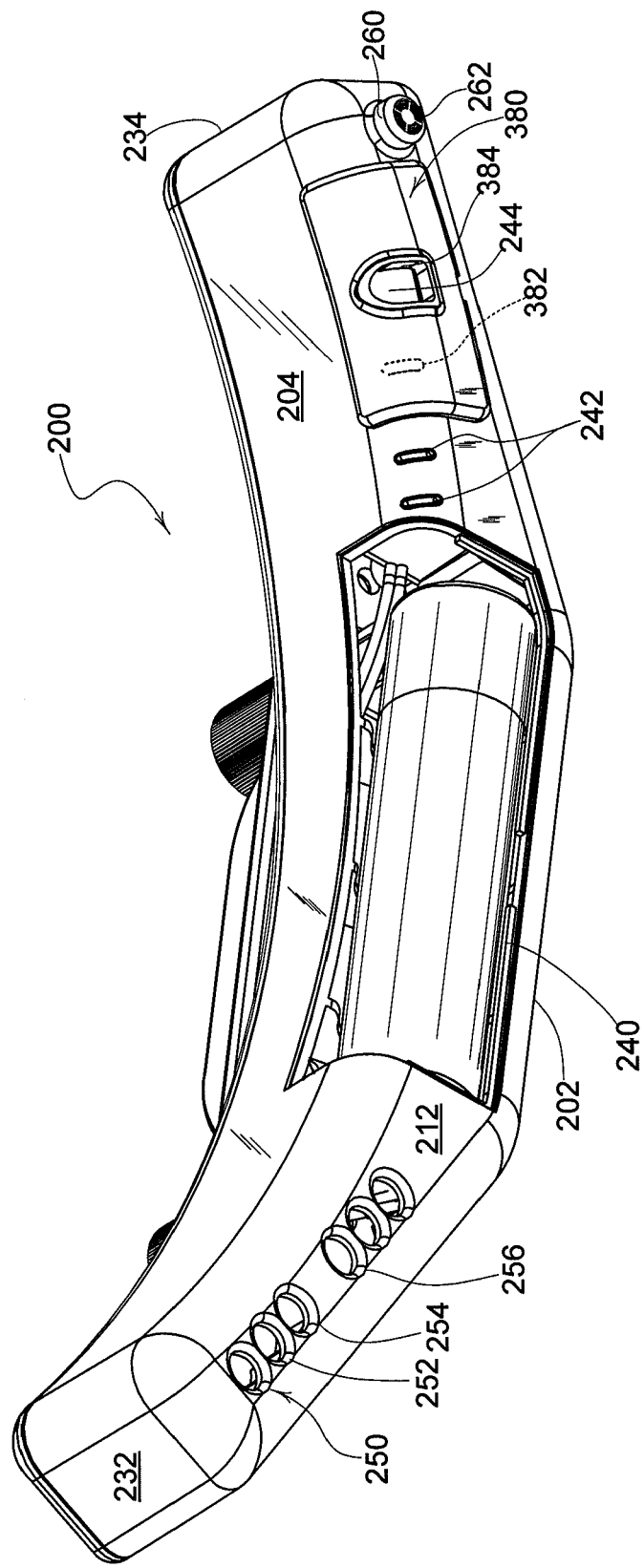
FIG. 10 shows a perspective view a the bottom and a back of the ventilation system embodiments of FIGS. 5A and 5B with a battery door removed therefrom.

With reference to FIG. 10 showing a perspective view of the bottom 212 and back 204 of the ventilation system 200, the base 222 may be provided with a plurality of detents 242 and an indicia surface 244. The detents 242 provide tactile and audible user feedback when using the ventilation system 200 while the indicia surface 244 provides visual feedback when using the ventilation system 200.

Figure 13:
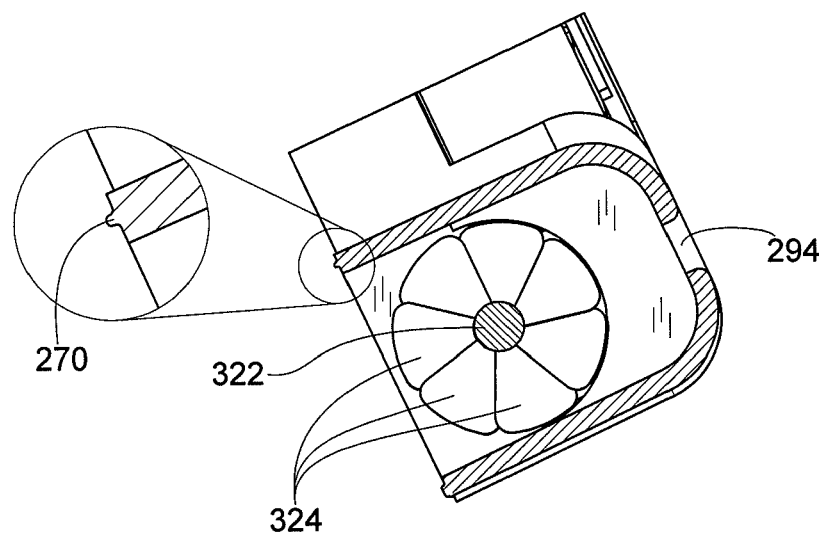
FIG. 13 shows a cross-sectional view of the ventilation system embodiments of FIGS. 11A and 11B taken across plane 13-13 detailing a fan assembly.

With continued reference to FIG. 10, the base bottom 212 may be provided with a plurality of intake ports 250 such as individual ports 252, 254, 256 located near, for example, the left side 232 of the base and on the bottom 212. Furthermore, the base 222 may be provided with a sensor protrusion 260 located near the right side 234. The sensor protrusion 260 may be provided with at least one sensor port 262 for providing fluid communication of air across the bottom 212. In one particular exemplary configuration, the intake ports 250 are separated from the sensor port 262 so that air flowing through the intake ports 250 does not cause a misreading of air near the sensor ports 262. The ventilation system base 222 may be formed with a welding rib 270 located on the top 224 as illustrated in FIG. 13.

With reference to FIGS. 9A and 9B, the enclosure top 280 is provided with a top 282, a bottom 284, a left 286 and a right 288 as illustrated. On the bottom 284, a first fastener protrusion 290 and second fastener protrusion (not shown) are formed for receiving a pair of identical posts 300. Each individual post 300 is provided with a base 302, a threaded portion 304 with a thread 306 formed therein, and a point 308 formed as illustrated in FIGS. 9A and 9B. The post base 302 is positioned in the first fastener protrusion 290 such that the threaded portion 304 protrudes from the top 282 of the enclosure top 280 (as illustrated, for example, in FIG. 8). The enclosure top 280 may be further provided with a plurality of ports 294 that extend thru the top 282 and the bottom 284 of the enclosure top 280.

The ventilation system 200 is further provided with a fan assembly 310 including a motor 312 and a fan 320. The motor 312 is provided with a shaft 314 (FIGS. 11A and 11B). The fan assembly fan 320 is provided with a shaft 322, a plurality of blades 324 and a hole 326 (FIGS. 11A and 11B). The plurality of blades 324 are formed on the shaft 322 and the hole 326 is formed in one end of the shaft 322. The fan assembly 310 is configured as illustrated and installed into the enclosure base 222. The support 330 of the fan assembly 310 may be configured as a rod having a cross hole 332 formed therein for receiving the shaft 322 as illustrated in FIGS. 11A and 11B.

Figure 12:
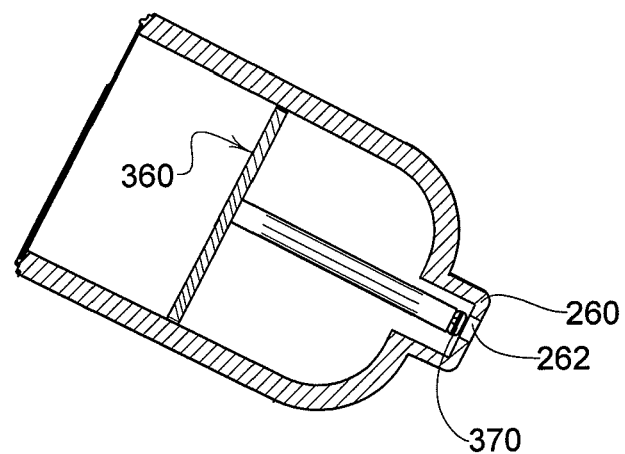
FIG. 12 shows a cross-sectional view of the ventilation system embodiments of FIGS. 11A and 11B taken across plane 12-12 detailing a humidity sensor.
Figure 14A:
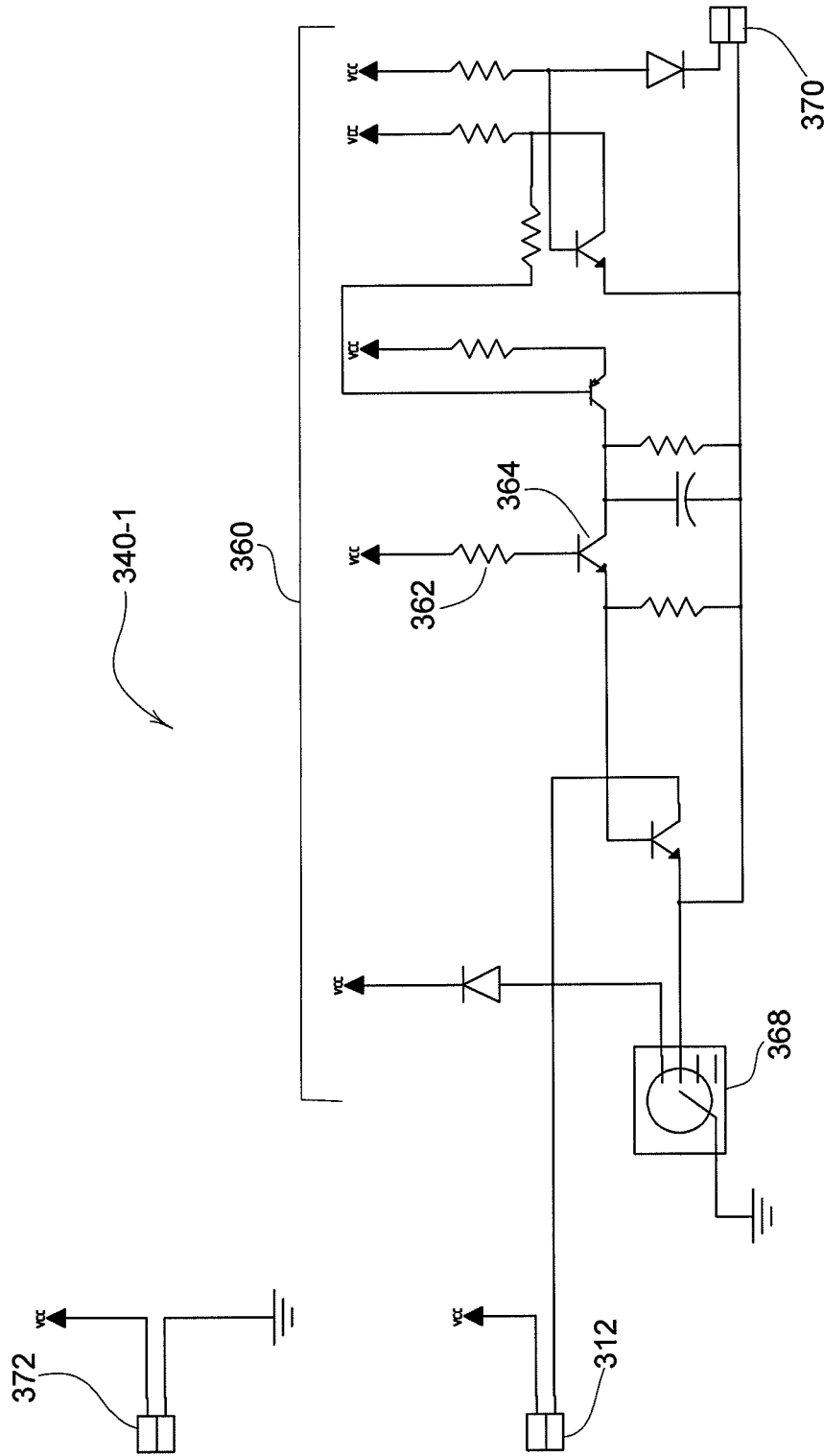
FIGS. 14A and 14B show exemplary electrical schematics of circuits for sensing humidity and activating a fan.
Figure 14B:
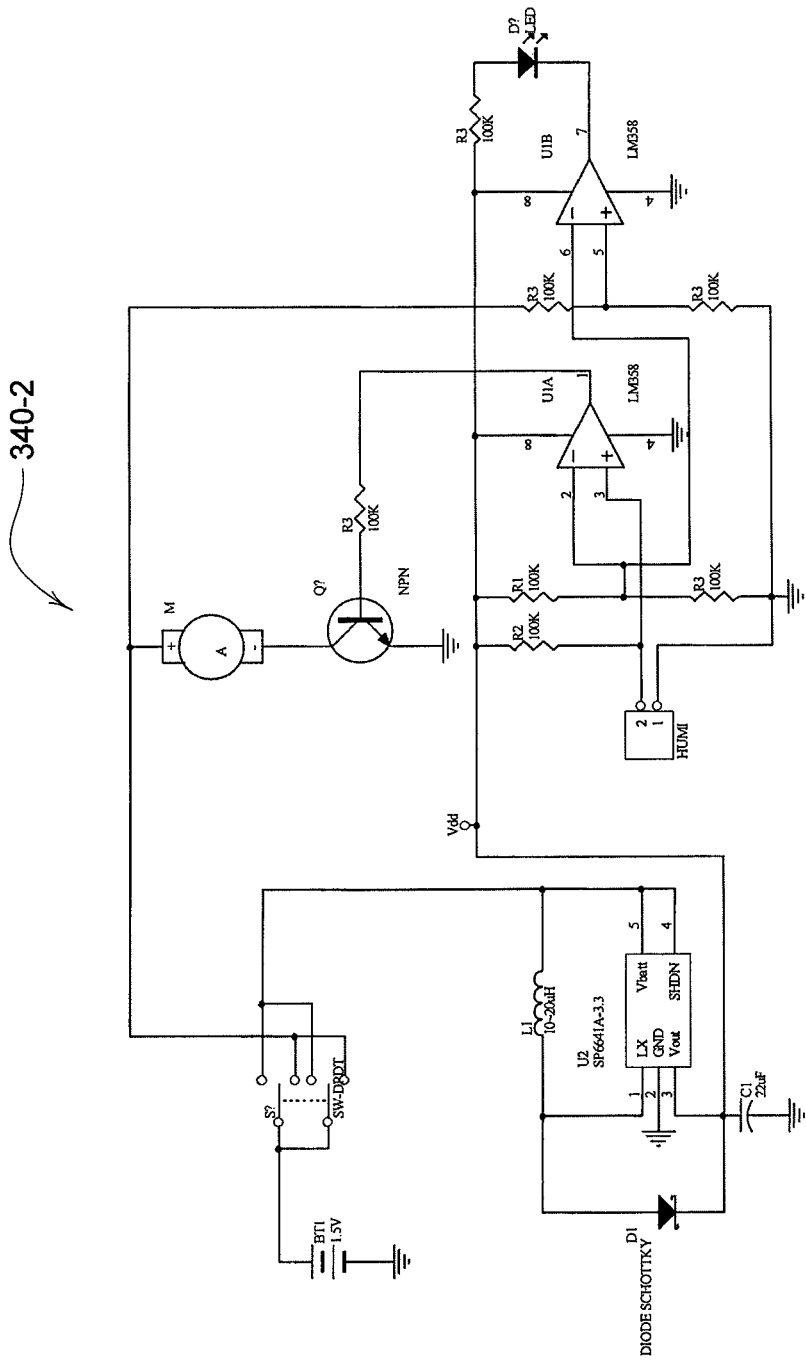

With continued reference to FIGS. 9A and 9B, the ventilation system 200 is further provided with an electrical assembly 340 including a first wire 342, a second wire 344, a third wire 346 (not shown), a fourth wire 348 (not shown), a negative terminal 350, a positive terminal 352, and a circuit board 360. The first and second wires 342, 344 electrically couple the circuit board 360 to the motor 312. The third and fourth wires 346, 348 electrically couple the terminals 350, 352 to the circuit board 360. Exemplary circuit boards 360 are illustrated schematically in FIGS. 14A and 14B and physically in FIGS. 9A and 9B. The circuit board 360 is provided with various components such as, for example, a resistor 362, a diode 364, a capacitor 366, a switch 368 and a humidity sensor 370. With reference to FIG. 12 showing a cross sectional view taken across plane 12-12 in FIGS. 11A and 11B, the humidity sensor 370 is positioned relatively close to, or in contact with, the sensor ports 262 formed in the sensor protrusion 260. This humidity sensor 370 is utilized in a process later described in detail for reading the humidity level of the air located in the goggles interior void. The electric assembly 340 is further provided with a battery 372. The battery 372 could be a N, A123, AAA or AAAA or another configuration.

With reference to FIG. 10, the ventilation system 200 is further provided with a switch interface 380. The switch interface 380 is provided with a protrusion 382 on a side adjacent to the enclosure base 222 for interacting with the detents 242. The switch interface 380 is further provided with an indicia window 384 for providing visual access to the indicia surface 244. By moving the switch interface 380 between three positions, the switch 368 is turns the fan off, activates the fan always or just when humidity reaches a threshold. In a process described later herein, the switch 368 controls the state of the ventilation system 200.

With reference again to FIGS. 9A and 9B, the ventilation system enclosure 222 is provided with a battery door 390. The battery door 390 interfaces with the battery opening 240 to enable the battery 372 to be secured such that the battery 372 interfaces with the terminals 350, 352 (as illustrated in FIGS. 10, 11A and 11B).

With reference to FIG. 9A, a first embodiment of the ventilation system 200-1 may be provided with a bridge 400-1. The bridge 400-1 defines a top 402 and an oppositely disposed bottom 404. The bridge 400-1 may be provided with a first fastener hole 406 and a second fastener hole 408 formed extending between the top 402 and the bottom 404 as illustrated in FIG. 9A. The first and second fastener holes 406, 408 are round as are matching holes 407, 409 in the enclosure top 280. With reference to FIG. 9B, a second embodiment of the ventilation system 200-2 has slotted fastener holes 406, 408 in the bridge 400-2 and the holes 407, 409 in the enclosure top 280. With slotted holes, the pair of posts 300 can move back and forth freely until the fasteners 422, 424 are tightened to allow accommodating a wider variety of frame tops 116. Some embodiments could have a hybrid where one set of holes 406, 407 is slotted and the other is round 408, 409 to still adjust, but in a different configuration.

Figure 5B:
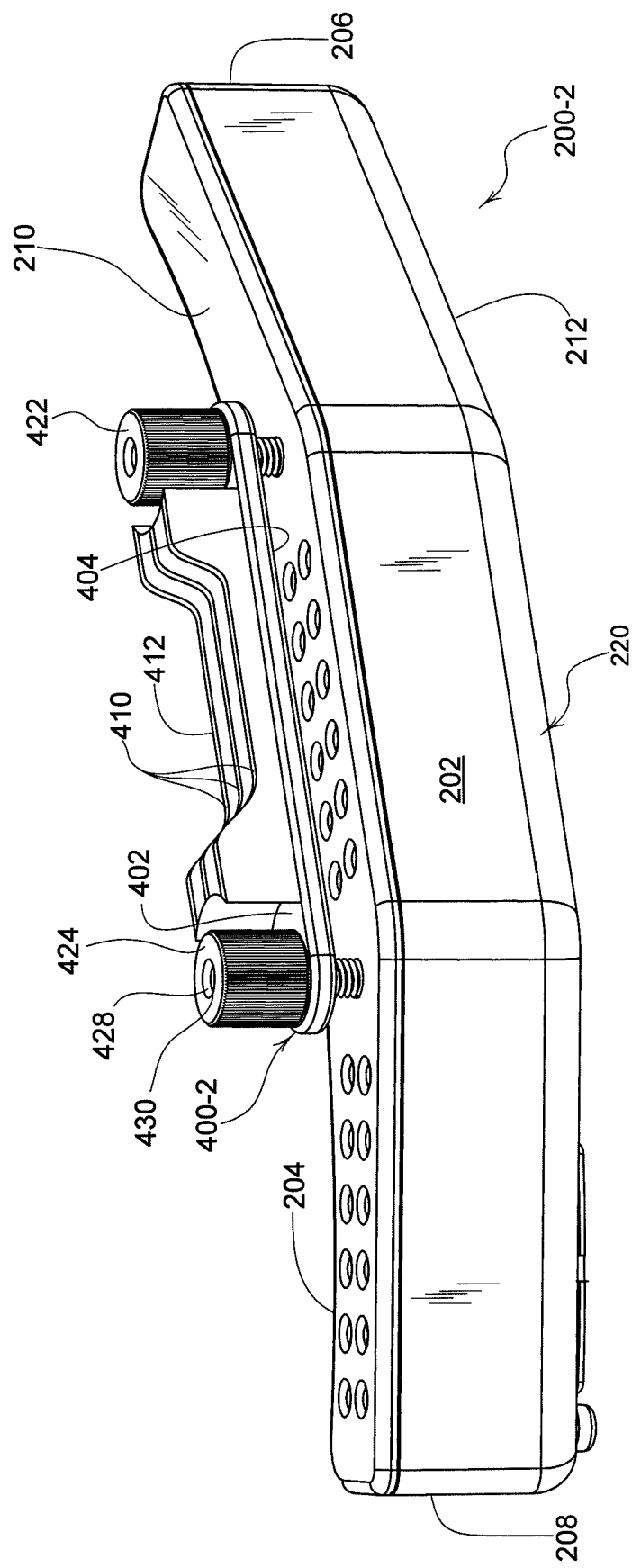
Figure 8:
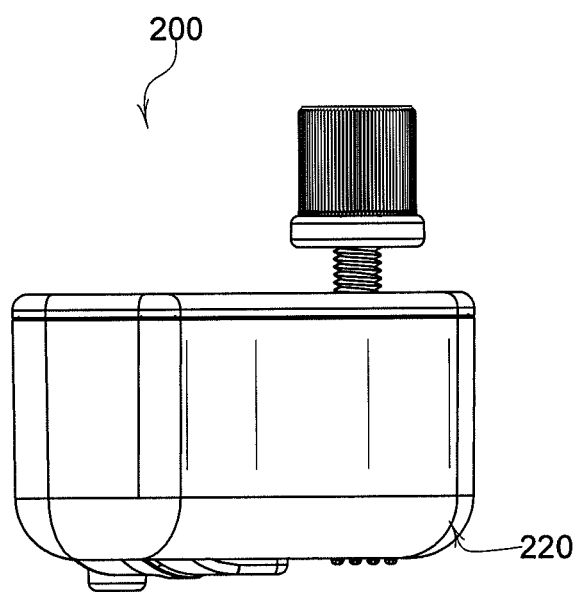
FIG. 8 shows a side elevation view of the ventilation system embodiments of FIGS. 5A and 5B.

With continued reference to FIGS. 5A and 5B, the bridge 400 may be provided with a plurality of ribs 410 such as individual rib 412 protruding from the bridge top 402. With reference now to FIGS. 7A and 7B, the bridge 400 may be provided with a plurality of ports 420. In one exemplary configuration, the plurality of ports 420 align with the plurality of ports 294 formed in the enclosure top 280. As illustrated in FIGS. 5A and 5B, the bridge 400 may be provided with a first fastener 422 and a second fastener 424.

First fastener 422 and second fastener 424 are identical, therefore described elements of second fastener 424 are inherently found in first fastener 422. Second fastener 424 may be provided with a barb 426 formed as illustrated in FIGS. 9A and 9B. The barb 426 is interfaced with the first fastener hole 406 (FIGS. 9A and 9B) such that the second fastener 424 is rotationally and nontranslatingly attached to the bridge 400. As used herein the term nontranslatingly means that the second fastener 424 remains attached to the bridge 400 and unable to be separated therefrom without damaging one of the two components. The second fastener 424 is further provided with a hole 428 with a thread 430 formed therein.

Having provided exemplary elements of one embodiment of the ventilation system 200, an assembly process will now be described. With reference to FIGS. 9A and 9B, the enclosure base 222 is positioned as illustrated and receives the fan assembly 310, the electrical assembly 340 (including the wires 342, 344, 346, 348, the negative terminal 350, the positive terminal 352, and the circuit board 360), the enclosure top 280 (with the posts 300 interfaced therewith), the battery 372 and the battery door 390. When assemblihg the ventilation system 200, the various components reference above are captured between the enclosure base 222 and the enclosure top 280 by ribs formed therein as illustrated. Once assembled, the enclosure 220 (FIGS. 5A and 5B) is closed by any of a variety of common manufacturing methods such as, for example, mechanical fastening, solvent welding, adhesive attachment, or ultrasonic welding via welding rib 270 (FIG. 13).

Having described an exemplary assembly process, the process of installing the present ventilation system 200 onto goggles 100 will now be provided. With reference to FIGS. 1 and 2, the ventilation system 200 is positioned adjacent to the lens back surface 134 and moved in a first direction D1 (FIG. 2) to cause the posts 300 (FIGS. 9A and 9B) to come into contact with foam commonly located at the top surface of the frame top 116. After contacting the foam, the ventilation system 200 is urged further in the first direction D1 causing the post point 308 (FIGS. 9A and 9B) to penetrate the foam and create a hole in the foam. Once the ventilation system enclosure top 210 is in contact with the frame top 116 as illustrated in FIG. 2, the bridge 400 is brought into contact with the posts 300 (FIGS. 9A and 9B) such that the fasteners 422, 424 can be threadingly engaged with the posts 300, respectively. This threading of the fasteners 422, 424 causes the frame 110 of the goggles 100 to be captured between the enclosure 220 and the bridge 400. The configuration of the enclosure 220 and the adjustable spacing of the posts 300 (FIGS. 9A and 9B) has been optimized to allow the present ventilation system 200 to be used in a variety of goggles (e.g. goggles 100) manufactured and distributed by a variety of manufacturers.

Once the present ventilation system 200 has been installed on the goggles 100, the user is able to put the goggles 100 over their eyes and experience the utility of the ventilation system 200. Commonly, the user will be participating in an outdoor activity (e.g. snow skiing or motor sports). While traveling at a relatively high speed, the user enjoys unobstructed vision because vapor has not condensed on the lens back surface 134 (FIG. 2). This unobstructed vision is owed mainly to the fact that air is forced through openings in the frame 110. When the user stops, the propensity for fogging increases because air is not being forced through the openings in the frame 110. As the user perspires, tears are generated by the eyes and humid air is exhaled and inadvertently displaced through the openings in the frame 110, the humidity level inside the goggles 100 can increase to where the dew point exceeds the temperature of the lens back surface 134 and vapor begins to buildup thereon. When the user has the present ventilation system 200 in an 'auto' condition via the switch interface 380, the ventilation system 200 responds to this increase in humidity by powering the fan assembly 310 (FIGS. 9A and 9B). The process of powering the fan assembly 310 automatically will now be described in further detail.

Figure 15:
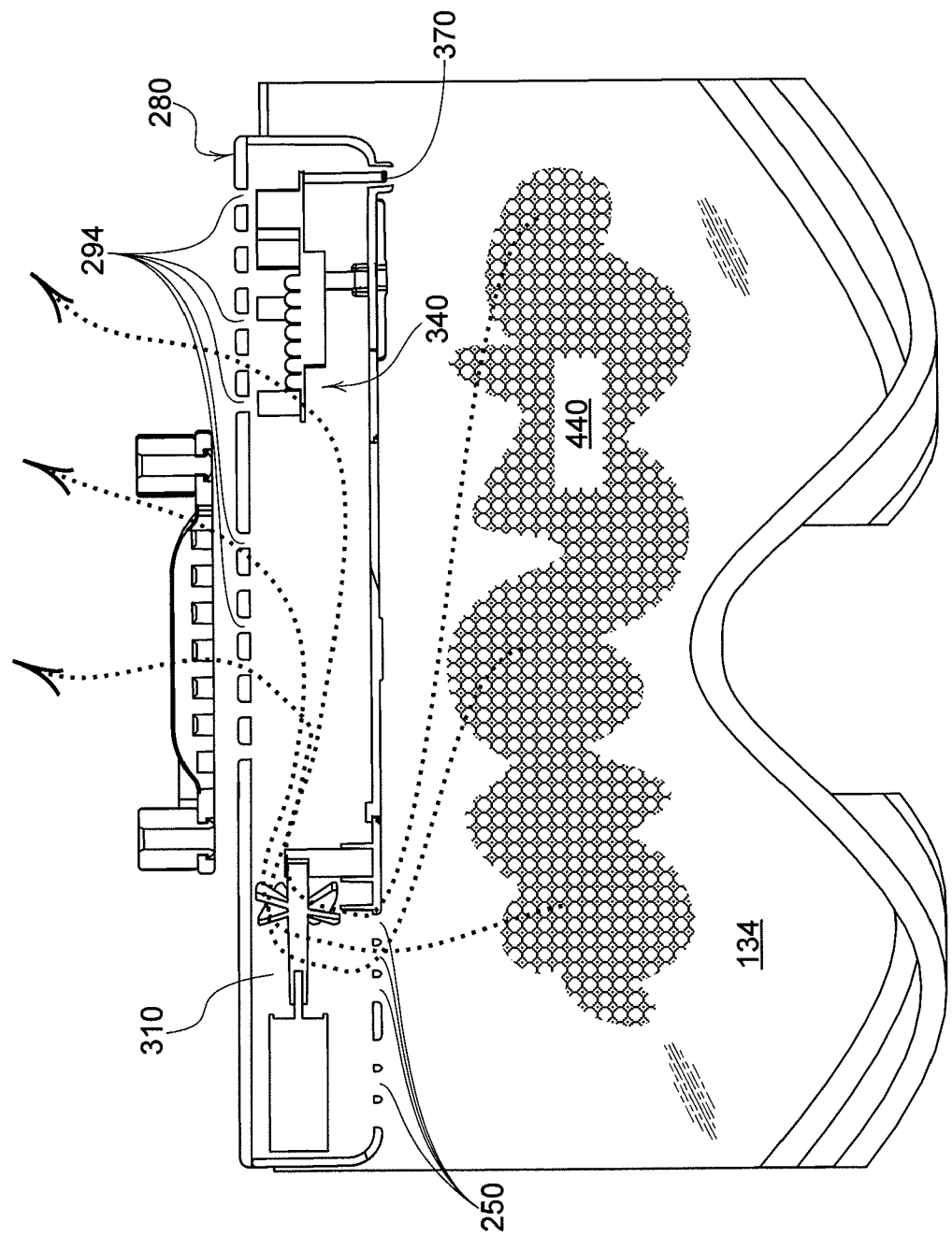
FIG. 15 shows an idealized cross-sectional view of the ventilation system and goggles taken across plane 15-15 in FIG. 6A.

With reference to FIG. 15 showing a cross-sectional view of the ventilation system 200 taken across plane 15-15 illustrated in FIGS. 6A and 6B, vapor 440 is sensed by the humidity sensor 370 which causes the fan assembly 310 to be activated via the electrical assembly 340. The vapor 440 is pulled from the interior portion of the goggles 100 past the plurality of intake ports 250 and ultimately ejected at the plurality of ports 294 formed in the enclosure top 280. In ejecting the vapor 440, the amount relative humidity in the interior portion of the goggles 100 is reduced. This reduction of vapor 440 continues until the humidity level has decreased enough to cause the electrical assembly 340 to temporarily suspend the operation of the fan assembly 310.

In one exemplary alternative embodiment, the switch interface 380 can be provided with three alternative locations. These three locations can include an 'off' position, an 'on' position, and an 'auto' position. In the off position, power is not being drained from the battery 372 and the system is essentially dormant. In the on position, the automatic operation of the electrical assembly 340 is essentially overridden and the fan assembly 310 is operated fulltime until the switch interface 380 is repositioned. In the auto position, the full benefit of the humidity sensor 370 is utilized and the system works in its optimal manner providing unobstructed vision in a variety of conditions.

With respect to the above description then, it is to be realized that the optimum dimensional relationships for the parts of the ventilation system for goggles, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the ventilation system for goggles.

Directional terms such as "front", "back", "top", "bottom", "left", "right", "interior", and the like may have been used in the description. These terms are applicable to the embodiments shown and described in conjunction with the drawings. These terms are merely used for the purpose of description in connection with the drawings and do not necessarily apply to the position in which the ventilation system for goggles may be used.

Therefore, the foregoing is considered as illustrative only of the principles of the ventilation system for goggles. Further, since numerous modifications and changes will readily occur to those skilled in the art, it is not desired to limit the ventilation system for goggles to the exact construction and operation shown and described, and accordingly, all suitable modifications and equivalents may be resorted to, falling within the scope of the ventilation system for goggles.

What is claimed is:

1. A ventilation system for readily and removably attaching to a frame of goggles, the frame comprising a top component that during use of the goggles is above a user's eyes, that reduces fogging in an interior portion of the goggles so as to provide a user wearing the goggles with unobstructed vision, the ventilation system comprising:
   a fan;
   a battery;
   an enclosure housing the fan and the battery; and
   an attachment system for readily and removably attaching said ventilation system enclosure to said frame, the attachment system comprising:
      a bridge;
      a first post having a first end fixedly attached to the enclosure and a second end protruding to the exterior of the enclosure;
      a first fastener interfaced with the bridge;
      wherein the first post is configured to extend through the top component of the frame of the goggles to couple with the first fastener, such that the top component of the frame of the goggles is disposed between the enclosure and the bridge so that the enclosure is positioned interior to the goggles, and
   wherein the ventilation system is configured to eject water vapor from the interior portion of the goggles to reduce relative humidity in the interior portion of the goggles.

2. The ventilation system of claim 1 and further wherein the fan is attached to a shaft that is oriented horizontally.

3. The ventilation system of claim 1 and further comprising:
   a hole formed in said enclosure; and
   wherein the first end of the first post is fixedly attached to the interior of the enclosure, the first post extends through the hole, and the first post is threaded on a portion of its exterior.

4. The ventilation system of claim 1 and further comprising:
   a slotted hole formed in said enclosure to allow the first fastener to move with respect to said slotted hole.

5. The ventilation system of claim 1 wherein said attachment system further comprises:
   a pair of fastener holes formed in the bridge; and
   a second fastener;
   wherein each of the first and second fasteners are interfaced with a respective fastener hole of the pair of fastener holes.

6. The ventilation system of claim 5 wherein each of the first and second fasteners are rotationally attached to said bridge.

7. The ventilation system of claim 5 wherein each of said first and second fasteners comprises a screw thread.

8. The ventilation system of claim 7 wherein each of said screw threads are disposed on an interior surface of a respective fastener hole.

9. The ventilation system of claim 5 wherein said bridge has a plurality of ports formed therein.

10. The ventilation system of claim 9 and further comprising:
    a plurality of ports formed in said enclosure;
    wherein at least one of said enclosure ports is aligned with at least one of said bridge ports.

11. The ventilation system of claim 1 and further comprising:
    a humidity sensor operatively associated with said fan.

12. The ventilation system of claim 1 and further comprising:
    a battery access formed in said enclosure; and
    wherein said battery is readily removable from said enclosure through said battery access.

13. The ventilation system of claim 1, wherein
    said first post comprises a distal end formed into a point.

14. A ventilation system for goggles that reduces fogging in an interior portion of the goggles, the goggles comprising a frame having a top component that during use of the goggles is above a user's eyes, so as to provide the user wearing the goggles with unobstructed vision, the ventilation system comprising:
    an enclosure comprising:
        a first distal end section;
        a second distal end section oppositely disposed from said first distal end;
        a mid-section disposed between the first and second distal ends, wherein the mid-section is forward of said first and second distal ends; and
        an intake formed in said first distal end section;
        a fan; and
        a humidity sensor adjacent to said second distal end section; and
    an attachment system for readily and removably attaching the ventilation system enclosure to a goggles frame, the attachment system comprising:
        a bridge;
        a first post having a first end fixedly attached to the enclosure and so that a second end of the post extends to the exterior of the enclosure;
        a first fastener interfaced with the bridge;
        wherein the first post is configured to extend through the top component of the frame of the goggles to couple with the first fastener, such that the top component of the frame of the goggles is disposed between the bridge and the enclosure so that the enclosure is positioned interior to the goggles, and
    wherein the fan is configured to eject water vapor from the interior portion of the goggles to reduce relative humidity in the interior portion of the goggles.

15. The ventilation system of claim 14 wherein said intake comprises a plurality of holes.

16. The ventilation system of claim 14 wherein said second distal end section comprises:
    a protrusion; and
    a port formed in said protrusion adjacent to said humidity sensor.

17. The ventilation system of claim 14 and further comprising:
    a battery access formed between said first and second distal ends.

18. The ventilation system of claim 14 and further comprising:
    a motor disposed between distal ends of the ventilation system, said motor comprising:
    a shaft end configured in an horizontal orientation;
    a connection end oppositely disposed from said shaft end;
    wherein said motor connection end is adjacent to said first distal end and said motor shaft end is directed towards said second distal end; and
    a fan attached to said motor shaft end.

\* \* \* \* \*